United States Patent [19]

Uriarte

[11] Patent Number: 5,043,888

[45] Date of Patent: Aug. 27, 1991

[54] FERTILITY INDICATOR

[76] Inventor: Jorge E. Uriarte, 13 Cornwallis, Irvine, Calif. 92714

[21] Appl. No.: 507,860

[22] Filed: Apr. 12, 1990

[51] Int. Cl.⁵ .......................... A61B 5/00; H01M 2/10
[52] U.S. Cl. ............................... 364/413.12; 128/738; 429/98
[58] Field of Search ................ 128/738; 364/413.12; 429/96, 97, 99, 100, 98; 439/500

[56] References Cited

U.S. PATENT DOCUMENTS

| | | | |
|---|---|---|---|
| 2,523,354 | 9/1950 | Butler | 429/98 |
| 4,151,831 | 5/1979 | Lester | 128/736 |
| 4,367,527 | 1/1983 | Desjacques | 364/413.12 |
| 4,465,077 | 8/1984 | Schneider | 128/738 |
| 4,488,560 | 12/1984 | Takamura | 128/738 |
| 4,530,366 | 7/1985 | Nessi et al. | 128/736 |
| 4,731,306 | 3/1988 | Dumbser | 428/98 |
| 4,771,791 | 9/1988 | Kubouchi | 128/736 |

FOREIGN PATENT DOCUMENTS 2079992 1/1982 United Kingdom .......... 364/413.12

*Primary Examiner*—Jerry Smith
*Assistant Examiner*—David Huntley
*Attorney, Agent, or Firm*—Alfred E. Miller

[57] ABSTRACT

A fertility indicator for storing a plurality of time measurements between consecutive menstrual periods by using a plurality of hours as a unit of count to optimize time measurements and output displays. The indicator uses a computer to analyze the menstrual cycles variables, by applying the Ogino's method and in combination with ovulation cycle variables, to project the fertile status for the present cycle, and by treating all of the stored cycles as the length of the present cycle. the fertile extensions are a true representation of user's cycle history in an ever renewing state as new data erases the oldest stored data. Arrangements are provided for data input protection and data retention.

4 Claims, 4 Drawing Sheets 5,043,888

FERTILITY INDICATOR

FIELD OF THE INVENTION

BACKGROUND OF THE INVENTION

Even though there are a number of birth control methods available, an ever increasing number women are reverting to abortions as birth control alternatives. Without exploring the moral implications of this issue, there is accordingly increased pressure to provide a birth control method that is totally innocuous, and that the majority of women of reproductive age can benefit from without any moral, social or health repercussions. Natural birth control methods fall into this category.

Many attempts have made in the past to provide a practical birth control method based on Ogino's method, more commonly know as the rhythm or calendar method. They have been used in combination with other physiological changes that normally occur before, during or after ovulation cycles for completeness. Many of them use a microcomputer with a number of input measurements of temperature or other bodily fluid changes, and in doing so they have elaborated a series of disciplines that makes them difficult to use.

For example in accordance with U.S. Pat. No. 4,770,186, a combination of saliva and vaginal mucus resistivity measurements are taken starting 5 days after the first day of menstruation and continuing for about 10 or more days. For each of these days and at the same hour the user must introduce into herself a vaginal probe and a salivary probe, take the measurements and either plot them or input them to a microprocessor based instrument. This method has the disadvantage that there must be a high degree of commitment required by the user to follow such a monthly discipline. In addition, the accuracy of the method in detecting ovulation is questionable since the fertile output projected by this method, not counting the days needed before ovulation, must extend for 4 days after ovulation, one may read a limitation on effectivity considering that the female egg has a maximum fertile life of 12 hours.

U.S. Pat. No. 4,465,077 discloses a method using basal body temperature measurements, menstrual cycle history, vaginal mucus change and gynecological disorder entry. Evaluation of inputs are many times subject to user criteria and some times will require lengthy training by a doctor or specialist, thereby increasing the possibility of reading errors. The menstrual cycle history is used to calculate an average figure. This average is not a true representation of the accumulated data but a tendency of it which will be further modified by error factors and other parameters to produce the final output. The method disclosed in this reference is hence quite complex.

U.S. Pat. No. 4,151,831 discloses the use of a combination of temperature measurements with the rhythm method. This reference states that ovulation occurs 14 days prior to menstruation, although researchers have found that ovulation cycle variations of 12 to 16 days are normal.

The above criteria are also applicable to other known techniques. Considering the seriousness of the problem, the prior art discloses only poor or no data protection from change or erasure that may occur by accidental key input or battery removal. It does not account for short measurements of time. For example, if an ovulation had occurred at 11:PM and then if intercourse takes place the morning after, there will be a high risk of pregnancy, but if intercourse takes place in the afternoon, it will be safe, even though both cases are on the same day. The reason for this is that the female egg has a maximum life of 12 hours after ovulation.

SUMMARY OF THE INVENTION

The purpose of this invention is to provide a simple, practical and economical devise that will inform the user of her fertile and infertile days with minimal user interface. It does not require a learning process or daily bodily checks of any kind. The user needs only to indicate the beginning of each menstrual period as they happen. The invention is based on the accumulation of user menstrual cycle history and uses computing means to analyze the menstrual cycles. By applying Ogino's method, more commonly known as the rhythm method, and in combination with ovulation cycle variables and with the optimization of outputs and time measurements by the use of hours instead of days, an accurate user fertile status will be projected.

The invention comprises an enclosure containing a plurality of input switches; an output including a plurality of color LEDs; a microcomputer with RAM memory to store menstrual cycles measurements, a ROM memory to store the working logic with programs for:
  a. Maintaining a time counter with a plurality of hours as a unit count for an accurate measurement of menstrual cycles and output of fertile extensions.
  b. Data input protection to avoid accidental entries by the use of software means: a personal code which is a sequence of numbers chosen by the user at initialization of the device; or hardware means: a key, cover or lock that makes it difficult to obtain accidental entry.
  c. Output of fertile days according to Ogino's method, and by combining the menstrual cycle variables with ovulation cycle variables, the projected fertile extensions will cover all of the user's menstrual cycle variables.
  d. Fan-out preprogram of menstrual cycles at the time of unit initialization for users who do not have any or enough history of their past menstrual periods. Preprograming is overwritten to the extent of available history.

Protection of RAM memory and internal timer from power loss by a battery replacement warning output, and by a built-in battery housing that accepts only a battery cartridge with a locking key and sliding contacts for maintaining uninterrupted power when exchanging batteries. A locking key prevents the battery from being pushed out from the device by any other object except by another battery cartridge with same key design.

BRIEF DESCRIPTION OF THE DRAWING

In order that the invention may be more clearly understood, it will now be disclosed in greater detail with reference to the accompanying drawing, wherein.

DETAILED DISCLOSURE OF THE INVENTION

DEFINITIONS

For convenience, as used herein, the following terms are defined and summarized to mean:

REALTMR—One byte memory variable that is incremented once every six hours.

BUFFER12—12 bytes of memory variables for the storage of menstrual cycle measurements, referred as BUFFER12(0) to BUFFER12(11).

GOR—A short program to turn on the green, orange and red LED's at the same time and turn them off after 0.5 second.

KEYVAL—One byte variable that stores key switch inputs.

POINTER12—One byte variable that points to the next available BUFFER12 location to be written into.

BUFFER4—4 bytes of variable memory that permanently stores the user secret code.

TBUFFER4—4 bytes of variable memory that temporarily stores an entered secret code to be compared later with BUFFER4.

ERROR—A short program to blink on the red LED three consecutive times each of 0.5 second duration.

BATTSENSE—One byte variable that is set to logic 1 when the battery is replaced.

FERTILEBEGIN—One byte variable that stores the beginning time of the fertile cycle.

FERTILEND—One byte variable that stores the ending time of the fertile cycle.

EXTERNAL CONFIGURATION

Figure 1:
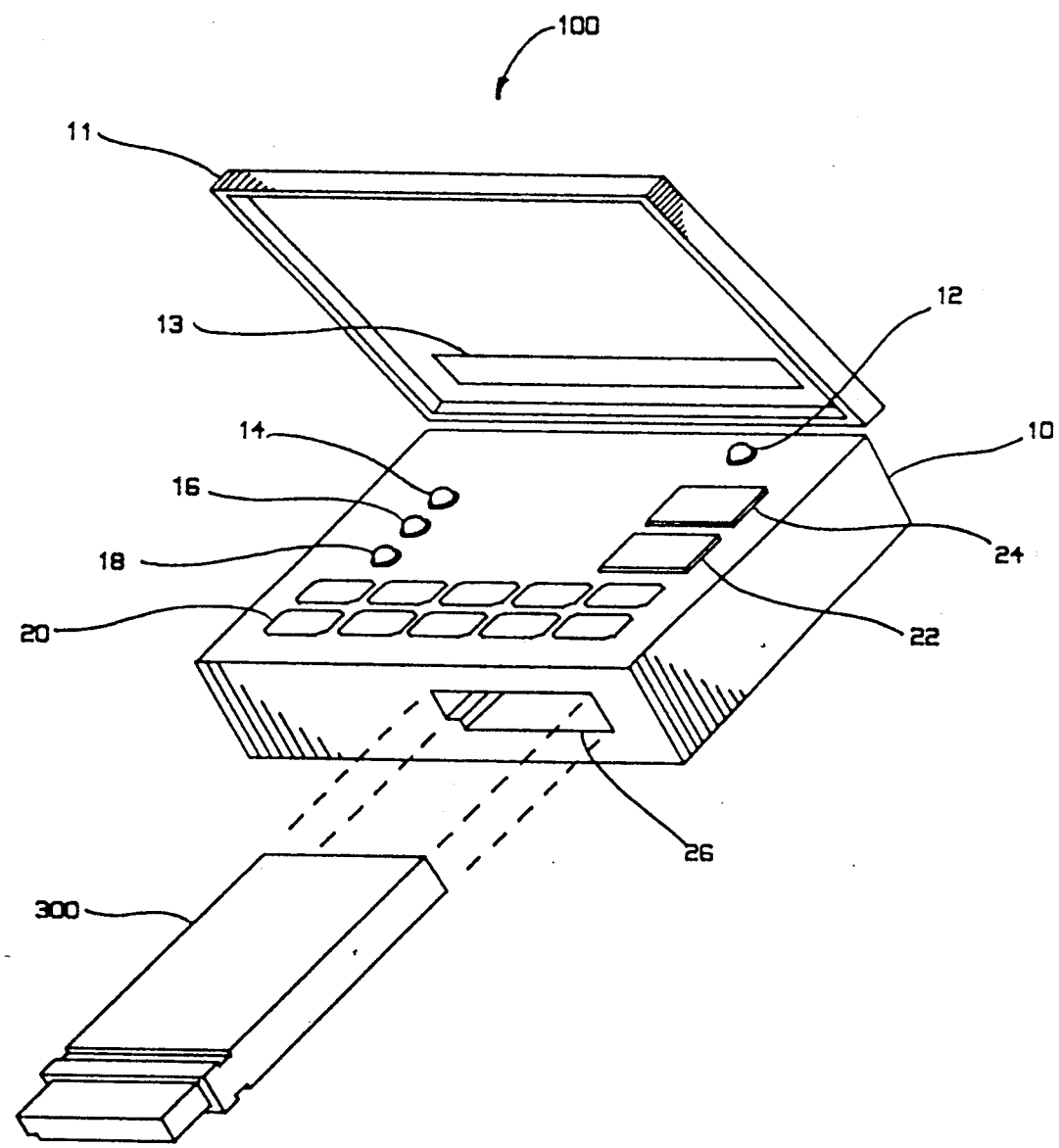
FIG. 1 is a view of one of the embodiments which embodies the invention into a hand held device.

FIG. 1 illustrates a preferred embodiment of the present invention in the form of a hand held, battery powered fertility computer. The enclosure 10 is a small plastic case which encloses the fertility computer 100 mounted on a printed circuit board, and the battery cartridge housing 26 with battery cartridge 300 for powering the computer. Enclosure 10 has a protective cover 11 with a user identification label 13 under the cover. A series of LED lights and momentary push-button switches is mounted on the outside of the enclosure and distributed as follows:

A yellow LED 12 controlled to flash for a short time only after a display function request, when it is time for a battery replacement.

A green LED 14 controlled to flash once for each non fertile day during the display function.

An orange LED 16 controlled to flash once for each variable fertile day during the display function.

A red LED 18 controlled to flash once for each fertile day during the display function.

An array of ten switches 20 for entering history information during initialization, and for entering the user's personal code for each menstrual period.

A switch 22 which serves as an enter key and a switch 24 which activates the display function. Instructions for use of device may be conveniently printed under the cover 11.

Figure 3A:
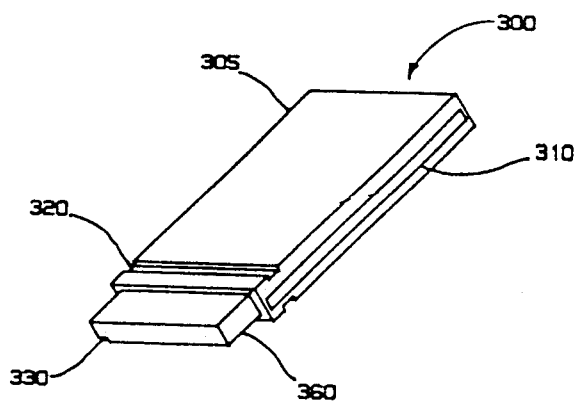
FIG. 3 (a), (b) and (c) shows the battery cartridge and battery housing latching mechanism arrangement.

FIG. 3a illustrates the battery cartridge 300 that has metal sliding contacts 310 extending along each side of its body 305, a pair of locking grooves 320 extending transversely of the body 305 adjacent one end thereof, a rear end key 360 projecting from the end of the body 305 adjacent the grooves, and a polarity orientation groove 330 extending longitudinally along one side of the body 305. The groove 330 fits a mating shoulder in the battery recess of the case, as depicted in FIG. 1, so that only a battery cartridge of predetermined shape can be used in the device of the invention. The contacts 310 constitute the terminals of the battery, and are adapted to engage internal contacts (not shown) in the battery receptacle of the case.

Figure 3B:
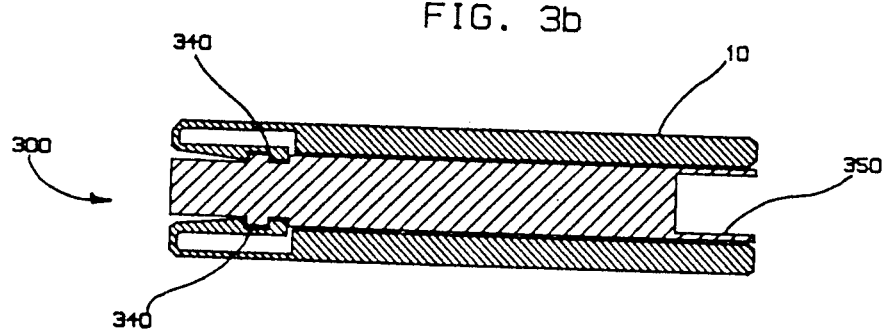

FIG. 3b is a cross sectional view of the battery cartridge 300 inserted in the case 10 and locked in place by the locking spring arms 340 of fertility computer case 10. The spring arms have tranverse ridges received in the grooves 320 of the battery cartridge, as illustrated, to inhibit its removal from the battery case. This view also shows the front key cavity 350 of battery cartridge 300.

Figure 3C:
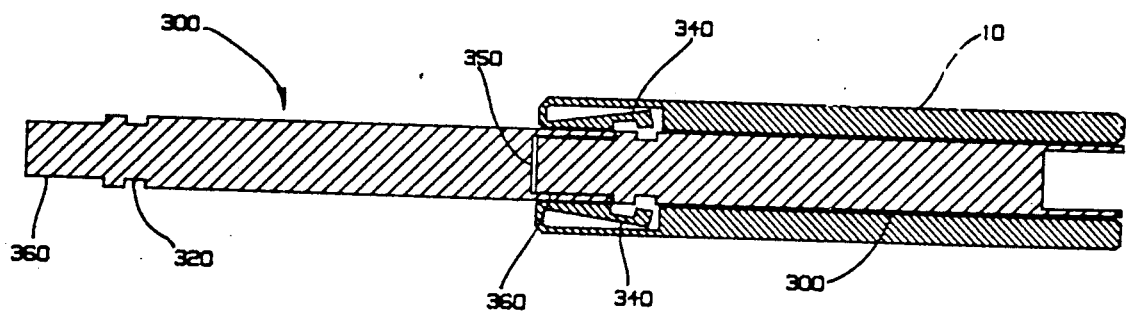

FIG. 3c is a cross sectional view illustrating the replacement of a battery cartridge inside fertility computer case 10. As the new battery cartridge 300 at the left side of the drawing is inserted in the direction of the arrow, with its key cavity 350 fit over the rear end key 360 of old battery cartridge 300 at the right side of the drawing, the peripheral regions of the forward end of the new cartridge force the locking spring arms 340 to sprung away from locking groove 320 of old battery cartridge until it is free and pushed out from cartridge housing cavity. For this purpose, the sides of the locking spring arms 430 in the battery recess, adjacent the opening thereof, are tapered to enable the arms to be pushed outwardly by the new battery. The new battery cartridge will become locked in place as it is pushed further into cavity and the locking groove thereof becomes aligned with locking spring arms 340.

FUNCTIONAL DESCRIPTION

Figure 2:
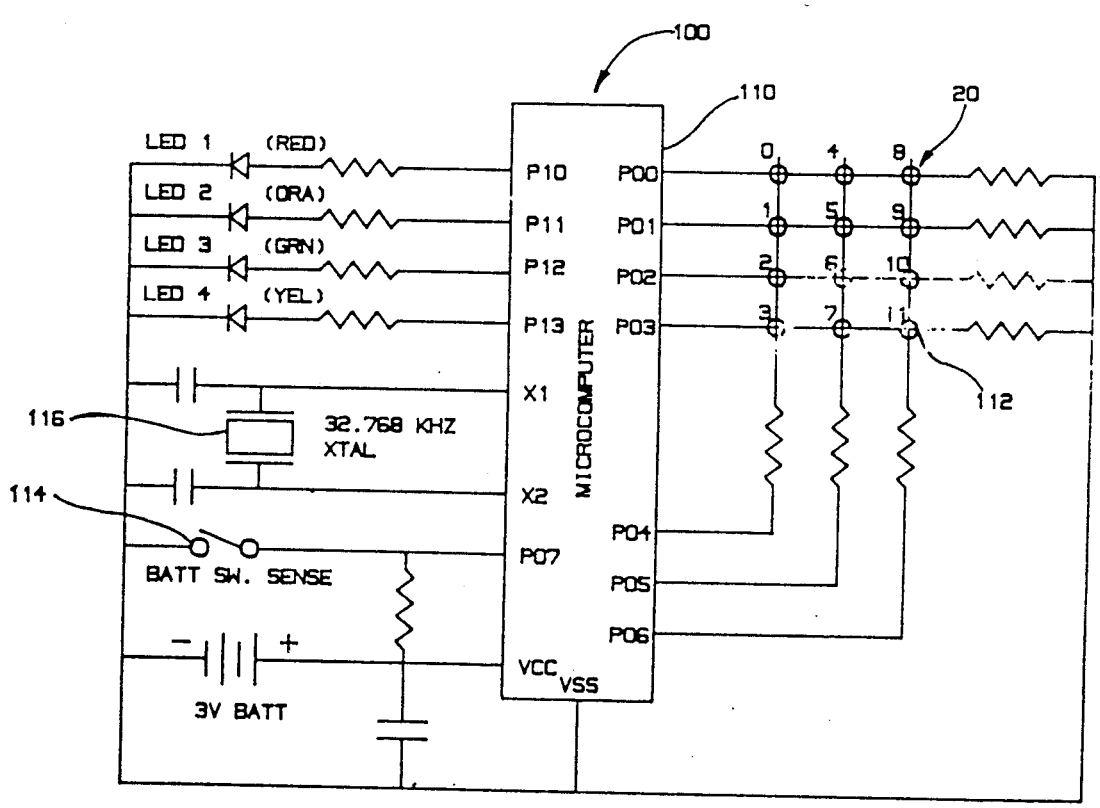
FIG. 2 is a detailed electrical schematic diagram of the present invention.

FIG. 2 is a schematic diagram of the fertility computer.

A computer such as a single CMOS chip microcontroller 110 that uses a few micro-amps to operate is the heart of fertility computer. It has internal ROM and RAM memory, and input and output control.

Figure 4:
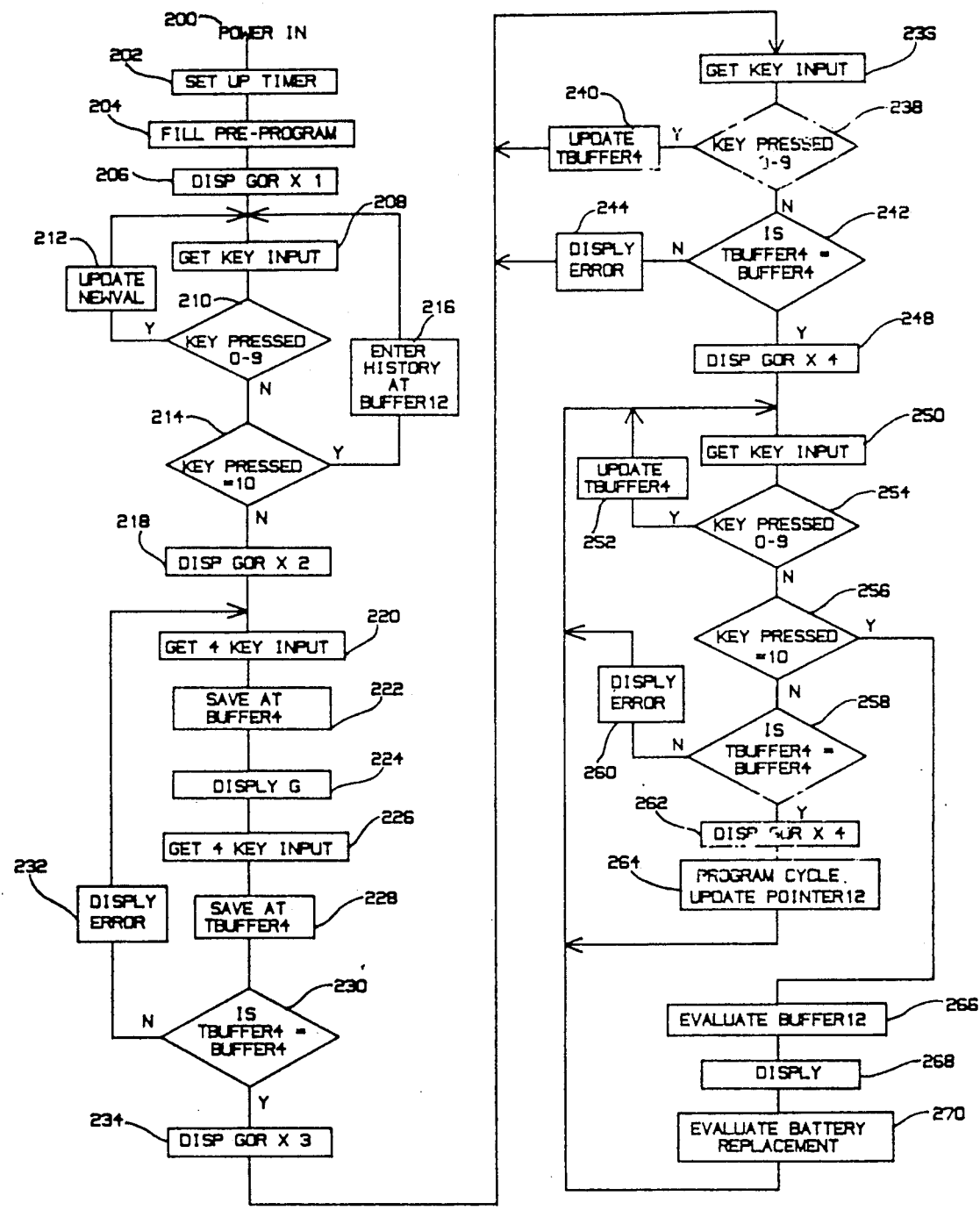
FIG. 4 is a flow chart showing the program for the present invention.

The fertility compute 100 is activated whenever battery cartridge 300 is inserted and latched into battery housing 26. Fig 4 shows the sequence of events that follow insertion of the battery. After power-in 200 the program initializes a real internal timer 202. The timer uses a 32.768 khz. crystal 116 to control its clock frequency, and this clock frequency is subsequently divided to accurately produce one count each 6 hours. The REALTMR variable is incremented once every six hours. This count is well adapted to the computer computations and the available storage area when considering that a day (24 hours) corresponds to 4 counts and that a memory storage byte may contain up to 256 counts, i.e. the equivalent of 64 days, far more than a normal menstrual cycle may last. The timer routine also checks the battery replacement sense switch 114. If the sense switch becomes closed due to the insertion of a new battery, this routine then sets BATTSENSED to logic 1. The switch 114 is hence positioned to close its contacts in response to each insertion of a battery in the case, and to open momentarily prior to the insertion of the new battery. For example, the sense switch may detect the insertion of the front end of a new battery into the case.

The program proceeds to the fill pre-program routine 204. Here the program fills a number of cycle lengths into BUFFER12 as follows:

BUFFER12(0)=96 (equ. to 24 days;96*6 =576/24 hours=24 days)
BUFFER12(1)=136(equ. to 34 days)
BUFFER12(2)=104(equ. to 26 days)
BUFFER12(3)=128(equ. to 32 days)
BUFFER12(4)=120(equ. to 30 days)
BUFFER12(5)=112(equ. to 28 days)
BUFFER12(6) to BUFFER12(11) are cleared.

This initialization allows a reasonable extension of fertile days for women who do not have a menstrual history and want to use the fertility computer right after the first menstrual cycle is entered. Note that the extreme preprogram cycles are at the beginning of BUFFER12, and they normalize towards 28 days as they go up in a pyramidal fashion. This is done so that the extreme preprogrammed cycles are overwritten first by the new real cycles entered by the user as new entries starts at BUFFER12(0).

Thereafter the program turns on the green, orange and red LED's once for 0.5 second (GOR 206) to indicate that user may now enter her history of menstrual cycles, if available. After a key input 208, the value of the key that was pressed is stored at KEYVAL and evaluated as follows:

a) If KEYVAL is between 0 and 9 (210), the KEYVAL value is added to NEWVAL; if NEWVAL was zero then KEYVA is multiplied by 10 before storing at NEWVAL.

b) If KEYVAL is 10 then the enter key 214 has been pressed. Now NEWVAL is multiplied by 4 and stored at BUFFER12(0), 216, and POINTER12 is updated to next BUFFER12. If POINTER12 was pointing to BUFFER12(11), then it will loop back to point to BUFFER12(0).

c) if KEYVAL is 11 then the display key has being pressed indicating the end of the menstrual cycle history entry even if none were entered. Now the GOR 218 is displayed twice to indicate that user must enter her personal code.

The program now receives 4 key inputs 220 in sequence and stores them at BUFFER4 (222). The green LED 224 is turned on for 0.5 second to indicate that the user must now reenter the same 4 key inputs 226, and they will be stored at TBUFFER4 (228). Now the program will compare the two sets of numbers 280. If they are different, it will display ERROR and go back to 220. If they are the same then GOR 234 is displayed for 3 times indicating that the fertility computer has been initialized and ready for use. Now the user must wait for her first signs of her menstrual period, upon which she will enter her personal code. After a key input 236, KEYVAL is evaluated as follows:

a) If KEYVAL is between 0-9 (238), then KEYVAL is stored at the next available location in TBUFFER4.

b) If KEYVAL is 10 or 11 then TBUFFER4 is evaluated against BUFFER4 242. The display function is not allowed until the start of the first menstrual cycle is entered. If TBUFFER4 and BUFFER4 are different then ERROR 244 is displayed. If they are the same then GOR 248 is displayed 4 times to indicate that user code has been accepted and REALTMR has been zeroed to start timing her first menstrual cycle.

The remainder of the program is an endless loop that switches between evaluating personal code entries to enter menstrual cycles and display function requests.

Thus, after a key input 250, KEYVAL is evaluated as follows:

a) If KEYVAL is between 0-9(254), then KEYVAL is store at next available location in TBUFFER4.

b) If KEYVAL is 10 then TBUFFER4 is evaluated with respect to BUFFER4 258. If TBUFFER4 and BUFFER4 are different then ERROR 260 is displayed. If they are the same then GOR 262 is displayed 4 times to indicate that user code has been accepted. REALTMR is saved in BUFFER12 at the location pointed by POINTER12; POINTER12 is updated and BUFFEWR12 is zeroed to start timing the next menstrual cycle.

c) If KEYVAL is 11 (256) then the display function is activated. Here the program 266 evaluates stored information at BUFFER12 and selects the shortest and longest menstrual cycle. These values are copied into FERTILEBEGIN and FERTILEND variables respectively. FERTILEBEGIN is decremented by 76 units. These units are a result of decrement by 14 days in accordance with Ogino's method, decremented by 72 hours which is the maximum life of the sperm and by 24 hours of ovulation cycle variable. FERTILEND is decremented by 14 days in accordance with Ogino's method, incremented by 12 hours which is the lifetime of the female ovum, and by 24 hour of ovulation cycle variable, for a total of 32 units of 6 hours each. Now FERTILEBEGIN and FERTILEND contain the beginning and ending fertile times in 6 hour units. These variables are decremented by the amount on REALTMR, and then any remainder is displayed 268 with a flash per every 4 counts (24 hours) with the corresponding LED color: green for the unfertile counts and red for the fertile counts; orange is displayed for the first 8 counts of fertile units and the last 8 counts of the fertile units, corresponding to the ovulation variables. If REALTMR is larger than FERTILEND then the green LED color is flashed once, indicating that user status is unfertile until the next menstrual cycle is programmed.

In use of the device, the first LED flash displayed shows the user her immediate fertility status, and subsequent flashes show the future status at 24 hours increments. The display status will vary every 6 hours. It is important for the user to learn her fertile status shortly before intercourse, especially at the threshold of the fertile and infertile cycles.

After the display function the program 270 evaluates POINTER12 as follows:

a) If POINTER12 value is less than 12 then the program loops back to get key input 250.

b) If POINTER12 value is 12, this means that there have been 12 menstrual cycles entries, equivalent to approximately one year time and for reliability purposes, the battery must be replaced even though it may last over 2 years of normal use. Then if BATTSENSE has been set to logic 1, which means that the battery has been replaced, the program loops back to get key input 250. If BATTSENSE is not set then the yellow color LED is flashed for 3 consecutive times at 0.5 second intervals to indicate that battery must be replaced. The program loops back to get key input 250.

While only one embodiment of the present invention has been shown and described, it will be obvious to those skilled in the art that many changes and modifications may be made thereunto without departing from the spirit and scope of the invention. For example REALTMR can be replaced by a full blown timer calendar, and rather than storing hourly counts on BUFFER12, with an expanded memory the date and time of the start of the menstrual cycle can be saved. Input can be made with the use of voice recognition integrated circuits, and outputs can be applied to LCD displays where a series of flashes, or a range of dates, or a bar graph may represent user fertile status. Other outputs can be applied to a buzzer or a speech synthesizer. Other possible embodiments of the present invention can be in the form of a watch that also performs normal watch time functions.

What is claimed is:

1. A fertility computer comprising:

a numeric keyboard having means for manually inputting times of occurrence of menstrual cycles of a user;

storage means for storing a plurality of the times of occurrence of menstrual cycles most recently input via said inputting means;

data processing means responsive to the times of occurrence of menstrual cycles stored in said storage means for providing the user with her current fertility status;

display output means for outputting user fertility status, said display means comprising means responsive to said data processing means for displaying first and second different displays corresponding to fertile and non-fertile statuses, respectively; and means responsive to a single predetermined input via said keyboard for controlling said display means to selectively display said first and second displays, whereby the display of said first and second displays corresponds to the user's fertility status at successive times, said fertility computer further comprising a casing having a battery compartment extending linearly through said casing, said compartment having opposed openings for receiving an operating battery and ejecting said battery, and a battery in said compartment having sliding contacts for maintaining uninterrupted power to said computer when exchanging batteries, said battery having a locking key for preventing the battery from being pushed out of said compartment by any other object than another battery cartridge having same key design.

2. In a fertility computing device having a computer for measuring and analyzing data which is indicative of user fertile status, the improvement comprising:

(a) a housing;

(b) an electrical power source inside said housing;

(c) switch means mounted on said housing and coupled to said computer for entering a user personal access code to indicate the commencement of the user's menstrual period, for entering data, and for entering requests to display fertility status, and first and second display means for indicating fertile and non-fertile status, respectively said computer comprising means responsive to a receipt of a request from said switch means for indicating fertile and non-fertile status by sequentially energizing said first and second display means to display fertility statuses of the user for successive equally spaced apart times, said power source comprising a battery cartridge having a key shaped portion, and further including a built-in battery compartment for accepting said battery cartridge, said compartment having locking key means and sliding contacts for maintaining uninterrupted power when exchanging battery cartridges, said locking key means preventing the battery cartridge from being pushed out from the housing by any other object except by another battery cartridge having a recess matching the shape of said key shaped portion.

3. A battery powered computer system comprising a housing, a computer in said housing, said housing having an opening extending therethrough for receiving a battery cartridge, and a first battery cartridge in said opening, said cartridge having terminals in the form of sliding contacts on the sides thereof, said opening having sliding contacts for engaging the sliding contacts of the cartridge for energizing said computer, said housing having a latch arrangement for holding said cartridge in said opening, said latch being releasable by the engagement thereof with a second cartridge of the same shape as said first mentioned cartridge for replacement of said first mentioned cartridge.

4. The computer system of claim 3 wherein said first mentioned cartridge has a key shaped projection on one end thereof, and a recess on the end opposite said one end and having the same shape as said key shaped projection.

* * * * *